United States Patent
Tocque et al.

(12) 
(10) Patent No.: US 6,509,153 B1
(45) Date of Patent: *Jan. 21, 2003

(54) GENETIC MARKERS OF TOXICITY PREPARATION AND USES

(75) Inventors: Bruno Tocque, Courbevoie (FR); Laurent Bracco, Paris (FR); Fabien Schweighoffer, Vincennes (FR)

(73) Assignee: Exonhit Therapeutics SA, Paris (FR)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 3 days.

(21) Appl. No.: 09/456,370

(22) Filed: Dec. 8, 1999

(30) Foreign Application Priority Data

Sep. 13, 1999 (FR) .............................. 99 11405

(51) Int. Cl.⁷ .................. C12Q 1/68; C07H 21/02; C07H 21/04; A01N 61/00; A61K 38/00
(52) U.S. Cl. ................. 435/6; 536/23.1; 536/24.3; 514/1; 514/14
(58) Field of Search ................ 435/6, 91.1, 91.2, 435/183, 69.1; 436/501, 94; 536/23.1, 24.3, 24.33; 514/1, 14

(56) References Cited

FOREIGN PATENT DOCUMENTS

| FR | WO 97 13877 A | 4/1997 |
|----|---------------|--------|
| FR | 2 775 984 A | 9/1999 |

*Primary Examiner*—B. L. Sisson
(74) *Attorney, Agent, or Firm*—Clark & Elbing LLP (57) ABSTRACT

The present invention describes new methods for the determination of the potential toxicity of test compounds, as well as the kits and tools for the implementation of these methods. The invention also describes methods for generating nucleic acid sequences that can be used as genetic markers of toxicity. The invention is based in particular on the creation of differential nucleic acid banks characteristic of situations in which cell viability and/or proliferation are deregulated, and on the demonstration that these banks can be used to evaluate the toxicity profile of compounds with reliability and high sensitivity. The invention is of special utility in the pharmaceutical industry for analysis of the toxicity profile of compounds involved in drug development and/or in pharmaceutical compositions.

25 Claims, 3 Drawing Sheets

A) Untreated cells

B) Ethanol-treated cells

C) Cyclosporine-treated cells

A) Untreated cells

B) Clenbuterol-treated cells

C) R-propranolol-treated cells

D) D,L-propranolol-treated cells

Figure 3

GENETIC MARKERS OF TOXICITY PREPARATION AND USES

This application claims priority from prior foreign application no. 99 11405, filed on Sep. 13, 1999 in France.

The present invention is related to the technical areas of biotechnology, medicine, biology and biochemistry. Its applications concern the fields of human, animal and plant health. More particularly, the invention sets forth new methods for determining the potential toxicity of test compounds, as well as the kits and tools for the implementation of these methods. The invention also describes methods for obtaining nucleic acid sequences that can be used as genetic markers of toxicity. The invention is of special utility in the pharmaceutical industry for analysis of the toxicity profile of compounds involved in drug development and/or in pharmaceutical compositions.

Toxicity is the major reason for abandoning candidate therapeutic molecules during preclinical and clinical development. To our knowledge, at the present time there are no tests by which to rapidly determine the toxicity profile of a compound in man. Yet the regulatory authorities require that new candidate drugs undergo toxicity, mutagenicity, carcinogenicity and teratogenicity testing in animals as well as clinical trials in man. These tests are long and costly and are only partially satisfactory. For example, animal toxicity is far from being a reflection of human toxicity. Furthermore, the small number of patients enrolled in clinical trials does not systematically allow identification of toxicities associated with a small, specific population. The development, perfection and use of such tests should make it possible to identify and remove toxic compounds from the development process as far upstream as possible. In this manner new drugs could be marketed sooner and at a lesser cost to drug companies and, in turn, to health care organizations and consumers. In addition, such tests might also make it possible to detect some toxicities which currently come to light only during the post-marketing period.

The tests which are currently available do not provide sufficient characterization of toxicity markers or the potential toxicity of compounds. Some tests in bacteria, such as the Ames test, or in yeast, such as the test described in U.S. Pat. No. 4,997,757, evaluate the mutagenic potential of compounds. These tests can only detect damage at the level of the DNA. Yet many drugs exert toxic effects without being mutagens and cannot therefore be flagged by tests such as these. Other tests, such as that described in application WO 94/17208, make use of certain known eukaryotic gene promoters or response elements from these promoters, induced under different conditions of stress, to characterize drug toxicity. However, the small number of such genetic markers and the process being measured (promoter activity) do not allow prediction of the potential toxicity of the compounds. What's more, these tests are difficult to implement because they involve the culturing of transformed cell lines comprising one or more genetic constructions.

The present invention now describes rapid, effective methods by which to determine the potential toxicity of test compounds, as well as the tools and kits for the implementation of such methods. In the context of the invention, the term "toxicity" refers to any adverse and/or side effect of a compound on the metabolism of a cell or a tissue such as, in particular, its mutagenic, carcinogenic or teratogenic potential, and more generally any alteration in metabolism that can result in a harmful effect of the compound on the cell or the tissue. The present invention is based more specifically on genomics and on the development of genetic markers of toxicity that can be used to predict the toxic potential of any type of compound on any type of cell. The present invention also sets forth new methods for obtaining nucleic acid sequences that allow determination of the toxicity of compounds (eg., genetic markers of toxicity), particularly compounds entering into drug development and/or pharmaceutical compositions.

The present invention is based in part on the demonstration that genetic markers can be created and used to evaluate the toxicity of test compounds. In particular, and in an advantageous manner, these markers can be used regardless of the toxic compound being tested, and regardless of the type of cell in which the test compound is being studied. Such markers, as well as the supports, kits and methods of the invention advantageously lead to the rapid generation of toxicity profiles that are particularly thorough and reliable. Furthermore, these markers, supports, kits and methods of the invention also make it possible to determine and assign a toxicity index to the test compounds.

In particular, the present invention demonstrates that there exist genetic events that are common to situations of toxicity and to cellular metabolic pathways induced in the absence of toxic compounds. Such genetic events can therefore be induced and then used as markers of toxicity. As will be described in detail herein, such markers can further be selected or modified for the constitution of improved banks allowing a more highly predictive diagnosis of the toxicity of a compound. More specifically, the present invention now shows that genetic markers induced in a cell in a situation where cell signalling pathways are deregulated, particularly a cell in which cell viability and/or proliferation are deregulated (for example, in a situation of apoptosis), can be efficiently used to characterize the toxicity profile of test compounds. In an advantageous manner, the invention also shows that these markers can be used in toxicity tests irrespectively of the type of compound and the type of cell used. The invention also provides for the constitution of differential banks of nucleic acids characteristic of deregulated cell signalling pathway(s), particularly situations in which cell viability and/or proliferation are deregulated, and demonstrates that these banks can be used for a reliable, highly sensitive evaluation of the toxicity profile of compounds.

One subject of the invention is therefore based more specifically on the use of genetic markers characteristic of situation(s) of deregulation of cell signalling pathway(s) (situation(s) of "deregulation") to characterize the toxicity profile of test compounds. The invention more preferably concerns the use of genetic markers induced in a situation of deregulation to characterize the toxicity profile of test compounds. The invention more preferably concerns the use of nucleic acid clones corresponding to genetic events, such as transcriptional and/or splicing events, that are characteristic of situations of deregulation, as genetic markers of toxicity.

The invention also concerns methods for analysis of the potential toxicity of a test compound, comprising at least one hybridization step between a) a sample of nucleic acids from cells treated with this compound and b) a preparation (for example, a bank) of nucleic acids corresponding to genetic events characteristic of situation(s) of deregulation, the hybridization profile indicating the toxic potential of the test compound.

The invention further concerns the kits for the implementation of these methods, as well as the compositions and nucleic acid banks comprising genetic markers of deregulation(s) of cell signalling pathways, and also the methods by which to generate such markers.

The present invention is therefore based in particular on the identification and development of genetic markers of toxicity that can be used for predictive toxicity testing of test compounds, or as targets for the study of the mechanisms of cell death or the research and development of therapeutic agents.

1. IDENTIFICATION AND DEVELOPMENT OF GENETIC MARKERS OF TOXICITY

Cell viability and differentiation are regulated by the balance that exists between mitosis and apoptosis. In the body, tissue homeostasis is also regulated by this equilibrium between cell proliferation and cell death. Alterations in this equilibrium form the basis of disease, whether they be related to an excess (neurodegenerative disorders) or to a defect in apoptosis (rheumatoid arthritis, cancer). The present invention is based in particular on the hypothesis that disturbances in this equilibrium can also be involved in toxic phenomena and that genetic markers characteristic of these events of deregulation of cell signalling pathways (especially cell viability and/or proliferation) might represent efficient markers of toxicity.

The present invention now shows that there are genetic events common to these situations of deregulation of cell signalling pathways, and to situations of toxicity induced by compounds. The present invention also provides for methods by which to identify, characterize, select and isolate nucleic acid clones corresponding to these genetic events, and shows that they can be efficiently used as genetic markers of toxicity. The invention also describes the establishment of banks of such clones, particularly on solid supports, and their use in methods for evaluation of the toxicity of test compounds.

2. DEFINITIONS

In the context of the present invention, the term situation of deregulation, or "deregulation", refers to any situation in which one or more cell signalling pathways are deregulated or altered, and in particular any situation in which cell growth and/or viability are deregulated. This therefore concerns any cell in which one or more cell signalling pathways have been altered, in particular induced or repressed, for example a situation of apoptosis, as will be described hereafter in further detail.

In the context of the present invention, the term "genetic event characteristic of a situation of deregulation" refers more specifically to any modification of gene activity, particularly of gene expression (enhancement or repression, inhibition or induction, etc.), post-transcriptional regulation (particularly splicing), replication, appearance of deletions, etc., characteristic of deregulation, i.e. induced in a cell in a situation of deregulation. It is understood that each individual genetic event characteristic of deregulation is not necessarily specific to this situation, in so far as some cell signalling pathways participate in a number of cellular processes. However, the nucleic acid banks described by the invention contain different clones and therefore effectively represent the genetic signatures characteristic of such situations.

The clones described by the invention more preferably correspond to transcriptional and/or splicing genetic events characteristic of deregulation(s). In the context of the invention, the term "transcriptional event" encompasses more specifically any activity of gene expression, i.e. the production of primary transcripts, premessengers and messengers from coding regions. The term "splicing event" refers more particularly to any splicing event related to a situation of deregulation, i.e. the appearance of specific splicing forms, the disappearance of specific splicing forms, or possibly the modulation of the quantity of splicing forms, etc.

The invention therefore describes the production of nucleic acid clones corresponding to such genetic events characteristic of situations where one or more cell signalling pathways are altered, and their use as genetic markers of toxicity. In the context of the invention, a nucleic acid clone corresponding to such a genetic event refers to any nucleic acid or nucleic acid fragment comprising at least one region whose sequence is specific to this event. For example, it may be any nucleic acid comprising a sequence specific for a splicing form or a deletant characterizing a situation of deregulation, or even a gene which is specifically regulated or expressed in a situation of deregulation. Such clones are therefore nucleic acids that can hybridize, in the nucleic acid test sample, with splicing forms characteristic of the situation of deregulation or with genes preferentially or specifically expressed in a situation of deregulation. Through hybridization, these clones thereby reveal the presence of targeted genetic events in a test nucleic acid population.

3. PREPARATION OF GENETIC MARKERS OF TOXICITY

As noted above, the present invention shows that genetic markers characteristic of situations of deregulation can be used as markers of toxicity, and in this regard it describes the development of methods by which to generate and isolate such markers.

One subject of the invention is therefore based on the methods by which to generate genetic markers of toxicity. The methods of the invention more specifically comprise the establishment of clones and nucleic acid banks characteristic of deregulation(s) in cell signalling pathway(s). These clones and banks can be generated in different ways, as described hereafter. Furthermore, the banks of the invention can contain variable quantities of nucleic acid clones. In addition, these banks are advantageously deposited on supports to facilitate hybridization and analysis of the hybridization profile.

The starting material used for the production of the clones and banks primarily comprises populations of nucleic acids derived from cells in a situation of deregulation, and populations of nucleic acids derived from cells in a control situation. In a more specific embodiment, the process of production of genetic markers of toxicity according to the invention advantageously comprises a hybridization step between a nucleic acid sample derived from a cell in a situation of deregulation, and a nucleic acid sample derived from a cell in a control situation. This hybridization step enables the generation of (banks of) nucleic acid clones characteristic of the cell in the situation of deregulation relative to the control situation.

The nucleic acid populations used are, for example, total RNA or messenger RNA from cells in a situation of deregulation and a control situation, or nucleic acids derived from this total or messenger RNA by reverse transcription, amplification, cloning into vectors, etc. These populations can be prepared by conventional methods known to those skilled in the art, such as reverse transcription, amplification, etc.

The choice of the situation or situations of deregulation, the control situation or situations, and the methods for production and isolation of the markers, is important because it determines the relevance of the markers generated, and therefore of the banks, and also their ease of use.

3.1. Starting Material

As indicated above, the genetic markers of toxicity according to the invention are generally prepared initially from nucleic acid preparations derived from cells in a situation of deregulation. It is understood that these markers, once isolated and characterized, can be reproduced or amplified by artificial means such as PCR, artificial synthesis (when the sequences are available), amplification in bacteria, replication of banks, etc., as illustrated hereafter.

As noted above, in the context of the present invention the term "situation of deregulation" refers to any situation in which cell growth and/or viability are deregulated, for example any cell in which at least one cell signalling pathway has been altered.

According to a specific embodiment of the invention, the cell in the situation of deregulation is a cell in which the expression of all or part of a gene involved in cell growth or viability has been modified.

According to another specific embodiment of the invention, the cell in the situation of deregulation is a cell in which the expression of all or part of a relevant oncogene or anti-oncogene has been modified.

According to another specific embodiment of the invention, the cell in the situation of deregulation is a cell in which the expression of all or part of a gene involved in apoptosis has been modified.

Apoptosis is a term familiar to those skilled in the art; it refers to the process of programmed cell death. Apoptosis encompasses all the mechanisms, genes and metabolic pathways that lead to cell death. Examples of factors that initiate or carry out apoptosis include the anti-oncogenes, Fas and TNF receptors, adaptors (particularly "death domain"), members of the bcl2 family, or caspases, which are involved in ontogenic morphogenesis, pathological deregulations and cell death.

Within the scope of the invention, a situation of apoptosis can be any situation involving initiation, execution or termination of apoptosis, i.e. a situation of apoptosis at any stage in the process of cell death, including very early stages in which only some metabolic pathways (or cell signalling pathways) have been altered, for example by activation, repression, stimulation, etc. The clones of the invention can therefore be produced from any cell in which at least one cell signalling pathway has been altered, particularly in which at least one apoptotic pathway has been initiated. These can be cells in which a metabolic pathway involved in apoptosis has been induced or stimulated, even if this induction or stimulation is carried out in sublethal conditions (i.e. not resulting in cell death).

In this regard, the cells can be in a natural situation of apoptosis, as for example a population of tumor cells, certain nerve cells in pathological situations, etc., or cells in which apoptosis has been artificially induced. In the latter case, the situation of apoptosis can be induced by different types of treatment, particularly by modulation of the expression of genes that initiate or carry out apoptosis.

In a particular embodiment, the genetic markers of the invention are produced initially from a population of cells in which a situation of apoptosis has been artificially induced, by the induction or repression of the expression of all or part of a gene that initiates or carries out apoptosis.

According to a preferred embodiment of the invention, the cell in a situation of deregulation is a cell in which the expression of all or part of an anti-oncogene (or tumor suppressor gene) has been induced or enhanced.

In an especially preferred embodiment of the present invention, the genetic events characteristic of a situation of deregulation are genetic events induced by modification of the expression of one or more genes that initiate or carry out apoptosis, particularly one or more tumor suppressor genes (or a functional variant of such genes).

This can particularly be any cell in which overexpression of an anti-oncogene has been induced. In particular, this can be a cell in which a gene construct has been introduced to induce or enhance the quantity of an anti-oncogene in this cell. Specific examples of anti-oncogenes (also called tumor suppressor genes) include p53 (Eliyahu et al., Proc Natl Acad Sci USA (1989) 86: 8763–7; Finlay et al., Cell (1989) 57: 1083–93); Rb (Lee et al., Science (1987) 235: 1394–9); p73 (Kaghad et al., Cell (1997) 90: 809–19); TUPRO-2 (U.S. Pat. No. 5,849,899); NHTS (U.S. Pat. No. 5,892,016); p15 (Hannon et al., Nature 371 (1994) 257); p16 (Ivison et al., Nature Genet. 371 (1994) 180); etc., but this list is not exhaustive.

A typical example of a situation of deregulation according to the invention is generated by the induction or enhancement of p53 expression. The p53 tumor suppressor gene, or anti-oncogene, is situated at the crossroads between cell life and death, negatively regulating cell growth by inducing cell cycle arrest at the end of the G1 phase. This cell cycle arrest is characterized by repression of the expression of genes involved in G1 to S progression and by induction of specific genes. Abolition of these p53 functions is one of the mechanisms involved in the development of a large number of tumors in which p53 deletion or mutations are observed. Overexpression of p53 can induce apoptosis in different cell types. This overexpression induced by infection with a virus permitting expression of wild type p53 forms is the basis for the gene therapy of cancer. Induction of p53 expression can also occur physiologically, particularly during restructuring of the mammary glands after lactation has ceased. Apoptosis induction by removal of serum, a situation which affects a large number of metabolic pathways, has also been reported to involve p53 stabilization.

p53 induction triggers programmed cell death in cells when DNA damage saturates cell repair systems. This apoptosis induction involves the Fas system and the caspases in particular, whose messengers must be spliced to isoforms that are competent for cell death.

The invention more specifically describes the use of genetic markers induced by p53 expression (in particular wild type p53) to characterize the toxicity profile of test compounds. The invention more preferably concerns the use of nucleic acid clones corresponding to genetic events, such as transcriptional and/or splicing events, induced by p53 expression (in particular wild type p53), as genetic markers of toxicity.

The invention more specifically describes the obtaining and use of cDNA clones corresponding to qualitative and/or quantitative genetic events that differ between control cells (for example growing cells) and cells engaged in apoptosis through induction of wild type p53.

It is understood that there are other possibilities by which to subject cells to a stress that can engage them in programmed cell death (apoptosis) or alter cell signalling pathways. The invention therefore also concerns the use of other cell models such as those based on inducible (or constitutive) expression of all or part of anti-oncogenes, promotors, initiators and mediators of apoptosis. Among these genes can be advantageously chosen RB, the retinoblastoma gene product; p73, a p53 homolog; myc; or any other protein or protein fragment capable of interfering with cell growth and viability. As noted above, this can also be a tumor cell or a degenerated nerve cell, for example.

Other types of starting material consist, for example, of samples containing cells in which proliferation has been deregulated by activation of oncogene cascades (such as the ras signalling pathway), inactivation of tumor suppressor genes, inhibition of apoptotic cascades, inhibition or activation or kinase-mediated pathways (such as p13 kinase which stimulates Akt protein), inhibition of gene expression by antisense RNA or oligonucleotides, etc. A specific example of cells consists of tumor cells obtained from tumor biopsies, in which case the genetic markers according to the invention are those characteristic of the tumor cell relative to a specimen of control tissue, particularly healthy tissue, obtained by biopsy.

Furthermore, the situation of deregulation can also be induced by one or more selected toxic compounds that act on cell viability via processes that alter genome integrity (genotoxicity), cell redox potential, cell surface receptor response, protein conformation or energy status. In particular, such compounds can be used in combination with the aforementioned induction methods based on modification of gene expression.

The cell population used to induce a situation of deregulation can be of diverse origin and nature, such as epithelial, hepatic, pulmonary, nerve, muscle, fibroblastic cells, etc. Preferably these are human cells. They can be primary cultures or established lines, in which deregulation is induced under the aforementioned conditions. They can also be tumor specimens which will contain cells in a situation of deregulation, or serum-deprived cells. As indicated below, the genetic markers of deregulation for use as markers of toxicity according to the invention can be produced from different cell types.

The control situation used generally corresponds to a population of cells of the same type as the cells used for the situation of deregulation, although different cell types can be used. The control situation can be a normal, quiescent or proliferative situation or even a situation of deregulation, but at a degree or stage less advanced than the reference situation of deregulation.

The situation of deregulation is typically a situation of induction of expression of a tumor suppressor gene such as p53 or Rb, and the control situation is a situation in which induction of this expression is absent, or at a lower level. In another example, the situation of deregulation is a population of tumor cells and the control situation is a population of the same but healthy cells. Specific examples of cells are given in the experimental section.

3.2. Production of Markers and Banks

As noted above, the process of production of genetic markers of toxicity according to the invention advantageously comprises a hybridization step between a nucleic acid sample derived from a cell in a situation of deregulation, and a nucleic acid sample derived from a cell in a control situation. This hybridization step enables the generation of nucleic acid clones characteristic of the cell in the situation of deregulation relative to the control situation.

The nucleic acid populations are, for example, total RNA or messenger RNA from cells in a situation of deregulation and a control situation, or nucleic acids derived from this total or messenger RNA by reverse transcription, amplification, cloning into vectors, etc. These nucleic acids can be prepared according to methods familiar to those skilled in the art. Briefly, these methods generally comprise lysis of the cells, tissue or sample and isolation of the RNA by extraction. In particular, this can consist of a treatment with chaotropic agents such as guanidium thiocyanate, which destroys the cells and protects the RNA, followed by RNA extraction with solvents such as phenol or chloroform. Such methods are well known to those skilled in the art (see Maniatis et al., Chomczynski et al., Anal. Biochem. 162 (1987) 156), and can be easily put into practice by using commercially available kits such as the kit US73750 (Amersham) for total RNA. The RNA used does not have to be perfectly pure, and in particular the presence in the preparation of traces of genomic DNA or other cell components such as protein, etc. is not a problem so long as they do not significantly affect RNA stability. In addition, in an optional manner it is also possible to use not total RNA preparations but rather messenger RNA preparations. These can be isolated either directly from the biological sample or from total RNA by means of polyT sequences, according to conventional methods. In this regard, messenger RNA can be obtained through the use of commercially available kits such as the kit US72700 (Amersham). The RNA can also be obtained directly from banks or from other samples prepared in advance and/or available in collections, and stored under suitable conditions.

The hybridization can be carried out under different conditions which can be adjusted by those skilled in the art. The hybridization preferably uses an excess of the nucleic acid population derived from the situation of deregulation relative to the nucleic acid population derived from the control situation.

Using the product of the hybridization reaction, two main types of approaches can be used to isolate the clones characteristic of deregulation according to the invention. The first, which is strictly quantitative, enables the generation of a nucleic acid preparation comprising all (or a significant part) of the clones resulting from a difference in the level of expression between the two situations. Such clones (and banks) are obtained by known subtractive hybridization methods consisting primarily of eliminating the hybrids formed during the hybridization step and keeping only non-hybridized clones characteristic of the deregulated situation relative to the chosen control situation.

In a preferred embodiment, however, a qualitative process is used for the generation of a nucleic acid preparation comprising all (or a large part) of the clones resulting from functional gene mutations characteristic of the deregulated situation relative to the chosen control situation. More particularly, such a qualitative bank comprises not the entire group of clones whose expression is modified, but for example clones corresponding to splicing or deletion events that differ between the two situations. Considering the role of alternative splicing in cell regulatory and transformation pathways, such preparations (and banks) advantageously comprise clones having an important functional value and therefore likely to reflect the genetic modifications involved in the situation of deregulation. Such clones therefore enable the constitution of banks with greater predictive power and the generation of more representative genetic markers. Such qualitative banks can be constituted by the isolation from the hybrids formed during the hybridization step of nucleic acid regions corresponding to differential splicing or to deletions. Depending on the methods used, these regions correspond either to unpaired regions or to paired regions.

These two approaches are described below in more detail.

3.2.1. Production and Use of Differential Quantitative Banks

In a first embodiment, the present invention therefore makes use of a differential quantitative bank, i.e. a bank comprising nucleic acid clones corresponding to genes whose level of expression is modified in cells in the situation of deregulation relative to a control situation. Such banks can also be derived from differential quantitative analyses, pooling sequences whose expression is increased or decreased in cellular deregulation phenomena. The methods to establish this type of bank are familiar to those skilled in the art and can be broken down into the following categories:

High Flow Sequencing Electronic Subtraction

This process is based on the random sequencing of a certain number of cDNAs. A computer search engine can then be used to perform a subtraction between the two situations under analysis.

Serial Analysis of Gene Expression (SAGE)

This process is based on the recognition of a signature associated with each cDNA by using restriction enzymes and oligonucleotide adaptors. This label corresponds to a part of the cDNA sequence (10 nucleotides long so as to unambiguously identify the corresponding cDNA). The labels are then assembled for sequencing and analysis (Velculescu et al., Science, 1995, 270: 484–487). This approach therefore represents a short-cut to systematic sequencing.

Nucleic Acid Arrays

This method is based on the application at more or less high density of nucleic acids such as oligonucleotides, PCR fragments or cDNAs on solid supports such as membranes, glass plates or bio-chips. Messenger RNA probes from the healthy or pathological samples are then used in hybridization to identify messengers that are overexpressed or underexpressed.

Differential Display

This method makes use of an oligo-dT primer and random primers to perform PCR on cDNA populations. The PCR products are then compared on very high resolution gels. Differentially expressed fragments are then isolated and heir presence confirmed by northern blot analysis prior to sequencing. Several variants of this method have been described (Prashar and Weissman, PNAS, 1996, 93: 659–663). These variants differ in terms of the primer and restriction enzymes and adaptor used. Like the SAGE method, they make use of the 3'-ends of cDNAs. This approach is made accessible by the existence of several commercially available kits.

Subtractive Cloning

This method is based on the elimination of cDNAs that are common to the two samples under comparison. Thus, different kits in which the "tester" cDNA is hybridized with an excess of "driver" cDNA are available (Clontech). The final product consists of a pool of PCR-amplified fragments derived from differentially expressed cDNAs, which can be cloned in a suitable vector for subsequent analysis. RDA (Representational Difference Analysis) is another method based on this principle of subtraction (Lisitsyn et al., Science, 1993, 259: 946–951).

The implementation of these differential analytical methods therefore enables the generation of quantitative banks and clones, i.e. comprising all the sequences whose expression is increased or decreased in cellular deregulation phenomenon or phenomena.

3.2.2. Production and Use of Differential Qualitative Banks

In another embodiment, the present invention advantageously uses a differential qualitative bank, i.e. a bank comprising nucleic acid clones of which at least part of the sequence corresponds to the sequence of the genes differentially spliced in the cells in a situation of deregulation. This type of bank therefore comprises sequences that are differentially spliced in deregulatory processes.

The use of this type of bank is particularly advantageous. In fact, the different cellular stresses leading to cell death or to other deregulatory phenomena involve initiators and mediators of signalling pathways and regulate key cell cycle components, including p53. Regulation of the level of expression of this protein occurs mainly through stabilization and transcriptional enhancement.

While Fas receptors, members of the bcl2 family and caspases are regulated at the transcriptional level, they are also regulated at the level of premessenger RNA maturation and splicing. This post-transcriptional regulation is critical because, from a same transcription event, it determines the creation of a pro- or anti-apoptotic form of each member of the concerned protein families. These transcriptional and splicing modifications are regulated by cell signalling and metabolism. The transcription and splicing regulatory factors which provide "trans" regulation of these key steps of gene expression are proteins whose own activity is regulated, notably by phosphorylation, according to the state of proliferation, differentiation and viability of the cell. The splicing program which is engaged during cell deregulation and which mobilizes different initiators and mediators of cell death therefore reflects modifications in cell signalling due to different damage. By affecting the transcriptional and splicing machinery, these modifications affect the expression of many genes which are not limited to the genes known to play a role as initiators or mediators of deregulation, but participate at different levels of the signalling cascades. Likewise, the cascades altered during oncogenesis, particularly by expression of splicing variants, mobilize markers whose expression is not restricted to tumors.

To take into account these phenomena and this complexity, and to thereby provide a more predictive evaluation of the toxic potential of a test compound, the process of the invention advantageously uses splicing events characteristic of deregulated situations, as genetic markers of toxicity.

To do so, the present invention uses, for example, differential qualitative nucleic acid banks produced according to "DATAS" methodology described in the unpublished international patent application PCT/FR 99/00547 and in U.S. Ser. No. 09/623,828, incorporated in the present specification by reference. In particular, such banks can be prepared by hybridization between the nucleic acid population derived from cells in a situation of deregulation, and the nucleic acid population derived from cells in a control situation, and isolation, from the hybrids formed, of the nucleic acids corresponding to differential splicing.

In this approach, hybridization is preferably carried out in liquid phase. Furthermore, it can be carried out in any suitable device such as tubes (Eppendorf tubes, for example), plates or any other suitable support commonly used in molecular biology. The hybridization is advantageously carried out in volumes of between 10 and 1000 $\mu l$, for example between and 500 μl. It is understood that the device and volumes used can be easily adapted by those skilled in the art. The quantities of nucleic acids used for the hybridization are also known to those skilled in the art. In general, microgram quantities of nucleic acids suffice, for example between approximately 0.1 and 100 μg. Furthermore, it is possible to use the nucleic acids in a driver/tester ratio ranging from approximately 50 to 0.02, preferably from 40 to 0.1. Even more advantageously, this ratio is preferably close to or greater than 1, advantageously between approximately 1 and approximately 10. It is understood that this ratio can be adapted by those skilled in the art according to the conditions of the process (available quantities of nucleic acids, physiological situations, purpose, etc.). The other hybridization parameters, including time, temperature and ionic strength, can also be adapted by those skilled in the art. As a general rule, following denaturation of the tester and driver, for example by heating, the hybridization is carried out for approximately 2 to 24 hours at a temperature of approximately 37° C. (possibly submitted to temperature spikes), and in standard conditions of ionic strength, which can range from 0.1 to 5 M NaCl, for example. Ionic strength is known to be one of the factors that determines the stringency of a hybridization, especially in the case of hybridization on a solid support. According to a specific embodiment of the invention, the hybridization is carried out in a phenol emulsion, for example according to the PERT method ("Phenol Emulsion DNA Reassociation Technique") described by Kohne D. E. et al. (Biochemistry, Vol. 16, No. 24, pp 5329–5341, 1977). The hybridization is avantageously carried out in a phenol emulsion maintained by thermocycling (temperature increase from approximately 37° C. to approximately 60–65° C.) and not by agitation, according to the method described by Miller and Riblet (NAR 23 (1995) 2339).

Any other hybridization method in liquid phase, preferably in emulsion, can be used within the scope of the present invention. Furthermore, the hybridization can also be done with one of the strands immobilized on a support. Advantageously, it is the driver that is immobilized. This can be done notably thanks to biotinylated primers or by any other immobilization technique known to those skilled in the art.

Using the nucleic acid populations generated by hybridization, the genetic markers of the invention (the clones characteristic of qualitative genomic alterations) can be identified by any method familiar to those skilled in the art. In the case of RNA/DNA heteroduplex, these regions are mainly regions of unpaired RNA (RNA loops) and can be identified and cloned by separation of the heteroduplex and the single-stranded nucleic acids (excess nucleic acids which did not react), selective digestion of the double-stranded RNA (domains participating in the heteroduplex), followed by separation of the resulting single-stranded RNA and the single-stranded DNA. In the case of heterotriplex, these differential splicing regions consist mainly of regions of double-stranded DNA and can be identified and cloned by treatment with suitable enzymes such as an enzyme that digests RNA, followed by an enzyme that digests single-stranded DNA. The nucleic acids so obtained are directly in the form of double-stranded DNA and can be cloned in any suitable vector.

It is understood that other specific variants and conditions for the isolation of nucleic acids, hybridization and obtaining of qualitative clones, are indicated in the not-yet-published application No. PCT/FR99/00547, incorporated in the present by reference.

These methods enable the generation of nucleic acid banks and clones corresponding to qualitative genetic markers of a situation(s) of deregulation.

As indicated in the experimental section, these nucleic acid preparations are especially useful markers to characterize the toxicity profile of compounds.

4. DIVERSITY OF THE BANKS

The aforementioned methods therefore enable the generation of groups of nucleic acid clones characteristic of situations of deregulation. Each method of preparation generates many clones which constitute banks. These banks can be used as is, deposited on supports, modified by the addition or removal of clones, or different banks can be pooled or control clones added, etc.

The banks provided for by the invention can comprise 10 to 50,000 clones, more generally 10 to 10,000 clones, and even more preferably 50 to 5,000 clones. The clones are generally deposited in a well-ordered fashion on one or more supports so as to facilitate analysis of the hybridization results. The support can be composed of glass, nylon, plastic, fiber, etc. or generally be any solid support suitable for the deposit of nucleic acids. The banks can be deposited on the supports by conventional methods known to those skilled in the art, as described for example in the international application No. PCT/FR99/00547.

The banks used can comprise both the nucleic acid clones corresponding to genes whose level of expression is altered in cells in a situation of deregulation (quantitative genetic markers) and the nucleic acid clones of which at least part of the sequence corresponds to genes that are differentially spliced in cells in a situation of deregulation (qualitative genetic markers). Thus, the genetic markers can be generated by different approaches, then pooled to obtain a response that is as predictive as possible. In this regard, it is also possible to use banks comprising clones derived from different situations of deregulation. For example, as noted above, the situations of deregulation can be induced in different manners (increased p53 gene expression, increased Rb gene expression, use of different cell populations, use of tumor cells, etc.). These different situations of deregulation do not always induce exactly the same genetic events, and therefore do not always produce exactly the same nucleic acid banks according to the invention. Although each of these banks can be used separately within the scope of the present invention, it is also possible to pool them on the same support (or on separate supports) so as to further increase the number of genetic markers of toxicity and thereby improve the predictability of the methods of the invention.

A subject of the present invention is therefore also based on a nucleic acid preparation comprising qualitative and quantitative genetic markers characteristic of cellular deregulation(s). A specific subject concerns a bank comprising genetic markers characteristic of different situations of deregulation. Another subject of the invention is any solid support on which at least two banks of nucleic acids characteristic of two situations of deregulation have been deposited. In this regard, the invention further concerns a process of preparation of a DNA chip used to determine the toxic potential of a test compound, comprising the application, on a solid support, of one or more nucleic acid preparations characteristic of situation(s) of deregulation.

Furthermore, in a preferred embodiment, use is made of nucleic acid banks refined through use by the selection of clones based on their actual involvement in toxicity phenomena. The initial banks can in fact comprise all the clones characteristic of genetic events of a situation of deregulation. Implementation of the diagnostic process set forth by the invention then makes it possible to observe that some of the clones hybridize very rarely, if ever, with the nucleic acid test samples. Such clones can eventually be removed from the bank in order to generate more specific, and therefore more universal and predictive banks.

Another advantageous subject of the invention is therefore based on a nucleic acid bank comprising nucleic acid clones corresponding to genetic events common to a situation of deregulation and a situation of toxicity.

Another subject concerns a method of preparation of banks of genetic markers of toxicity, comprising hybridization between a nucleic acid population derived from cells in a situation of deregulation, and a nucleic acid population derived from cells in a control situation, isolation from the hybridization product of clones characteristic of the situation of deregulation, and hybridization of the clones obtained with a nucleic acid sample derived from cells in a situation of toxicity. The above process advantageously further comprises a selection step, comprising hybridizing the bank with different nucleic acid samples derived from cells in a situation of toxicity induced by different compounds, and identification of the clones in the bank that hybridize most frequently with said samples.

More specifically, the present invention now describes the identification and characterization of such clones, which can be used as genetic markers of toxicity.

One of the major applications of the identification and cloning of these genetic markers concerns the evaluation of the toxic potential of a test compound. This evaluation can be carried out by hybridizing a probe corresponding to the messenger RNA of a cell culture treated with this product, with one or more banks of signatures characteristic of situation(s) of deregulation, such as those described above. This application is described in more detail below.

5. METHODS OF ANALYSIS AND DIAGNOSIS OF TOXICITY

The invention therefore also concerns a method for analysis of the toxic potential of test compounds, using the aforementioned genetic markers. In particular, the invention allows to determine the toxic potential of any compound by hybridizing a sample of nucleic acids from cells treated with this compound, with the aforementioned genetic markers, the observed hybridization profile indicating the toxic potential of the compound. To this end, the genetic markers used are preferably combined into banks so that the response can be as predictive as possible. One of the advantages of the present invention also concerns the large number of markers used, which makes the information obtained even more predictive. The predictive nature of the information is further strengthened by the type of markers used and prepared.

A specific subject of the invention is based on a method of analysis of the toxic potential of a test compound, comprising at least one hybridization step between a) a nucleic acid sample from cells treated with this compound and b) a nucleic acid bank corresponding to genetic events characteristic of situation(s) of deregulation of cell signalling pathway(s), the hybridization profile indicating the toxic potential of the test compound. In particular, the greater the number of hybridization-positive clones, the greater the potential toxicity of the test compound.

The analysis of the toxicity profile of the compound is more generally done by comparing the hybridization profile on the bank of a nucleic acid sample from cells treated with this compound, with that of a nucleic acid sample from cells not treated with the compound. This comparison makes it possible to demonstrate a difference between the number of hybridizing clones in the toxic situation and in the control situation, by which a toxicity index for the test compound can be established.

More specifically, the invention therefore concerns a method of analysis of the toxic potential of a test compound, comprising at least  a hybridization step between a) a nucleic acid sample from cells treated with this compound and b) a nucleic acid bank corresponding to genetic events characteristic of situation(s) of deregulation of cell signalling pathway(s),  a hybridization step between c) a nucleic acid sample from cells not treated with this compound and b) a nucleic acid bank corresponding to genetic events characteristic of situation(s) of deregulation of cell signalling pathway(s),  comparison of the hybridization profiles obtained indicates the toxic potential of the test compound.

The hybridization profile can be detected by any method familiar to those skilled in the art, and particularly by labelling of the nucleic acid test samples and detection of the label in the bank. Thus, the invention more specifically concerns a method of analysis of the toxic potential of a test compound comprising at least the separate hybridization between a) labelled nucleic acid probes corresponding to RNA from cells not treated and cells treated with said test compound and b) a nucleic acid bank corresponding to genetic events, particularly transcriptional and/or splicing events, characteristic of deregulation(s), the hybridization profile indicating the toxic potential of the test compound.

The nucleic acids can be labelled by any method known to those skilled in the art, particularly through the use of radioactive, fluorescent, enzymatic or colorimetric labels. In general, radioactive labelling is used and the hybridization is visualized by detection of radioactivity on the support. Fluorescent labelling can also be used, in which case the hybridization is visualized by detection of the fluorescence emitted on the support.

As indicated above, in the methods set forth by the invention, the nucleic acid banks corresponding to genetic events characteristic of deregulation(s) can be, in particular, nucleic acid banks characteristic of situations of deregulation of cell growth and/or viability. More specifically, these are nucleic acid banks characteristic of cells in a situation of deregulation of cell growth, notably transformed cells, tumor cells in particular.

In the methods of the invention described above, the nucleic acid banks are more preferably nucleic acid banks corresponding to genetic events characteristic of alterations in signalling pathways induced by the expression of all or part of a tumor suppressor gene, preferably p53. In particular these are banks characteristic of apoptosis induced by a tumor suppressor gene, preferably p53. The results presented in the examples demonstrate in particular that, through the use of a specific differential qualitative screening strategy, a situation of apoptosis resulting from induction of p53 protein expression leads to many modifications in splicing, in addition to quantitative modifications related to transcriptional regulation of different genes. The invention shows that probes from cells treated with different toxic compounds hybridize with clones from banks derived from quantitative and qualitative screening prepared from control cells, on the one hand, and from cells in which wild type p53 expression is induced, on the other hand. This indicates that the transcriptional and splicing events are common to toxic situations and to situations where wild type p53 protein expression is induced. Moreover, the results obtained also show that when the treated cells are of the same type as those in which p53 expression has been induced, the probes prepared from the messenger RNA from cells treated with increasing concentrations of the toxic compounds hybridize a larger number of clones in the quantitative and qualitative banks when the concentrations are high, and therefore the toxicity important. This demonstrates that there is a correlation between the level of toxicity and the hybridization profile on the banks of the invention.

It is clear however that the application of the methods, kits and banks of the invention is not restricted to a specific cell type. In particular, it is not restricted to tests of products on the same cells as those from which the quantitative or qualitative banks and clones are derived. In fact, the results presented show that the clones of the invention advantageously enable a diagnosis of toxicity independent of the toxic compound and the type of test cell.

In a specific embodiment of the methods of the invention, the cells treated or not treated with the test compound and the cells used to generate the banks are of a different type.

More specifically, the cells treated or not treated with the test compound can be of different origin and type. They are preferably mammalian cells, even more preferably human cells. They can be primary cultures or cell lines. The cell type used, its concentration, density and physiological state (resting, stimulated, etc.) can be chosen by the user of the methods of the invention according to the test compounds and desired applications. The cells can also be cells extracted from organs or tissues of animals treated or not treated with the compound.

The test compound can also be highly varied in nature. For example, it can be an individual compound or a mixture of compounds. The compound can be chemical or biological. In particular, it can be a peptide, polypeptide, nucleic acid, lipid, carbohydrate, a chemical molecule, plant extract, combinatorial libraries, etc. The test compound can also be a treatment applied to the cells, such as irradiation or UV. To implement the process of the invention, the test compound can be applied at different concentrations chosen by the user. Furthermore, the nucleic acid samples derived from the treated cells can be prepared at various time points after treatment with the compound. In this way, kinetic studies can be carried out as needed.

The nucleic acids and corresponding probes are prepared by conventional methods. Hybridization can then be carried out, also under conditions that can be adapted by those skilled in the art and by the user. In this regard, the hybridization can be carried out under high, intermediate or low stringency, depending on the desired level of sensitivity, quantity of available material, etc. Furthermore, according to the present invention the hybridizations between the bank and the probes can be homologous (when the bank and probes are composed of nucleic acids from the same species, for example human) or heterologous (when the bank and probes are composed of nucleic acids from different species, for example a human bank and probes prepared from material derived from another mammalian species). Although the banks and probes are preferably constructed from material of human origin, it is in fact possible to use other sources, particularly for the probes (for example, murine origin). For such heterologous hybridizations, the hybridization conditions can be adjusted by those skilled in the art according to conventional techniques, particularly by decreasing the hybridization temperature and/or by increasing the salt concentration of the hybridization buffer.

6. DETERMINATION OF A TOXICITY INDEX

An advantage of the methods of the invention is based on the possibility of determining a toxicity index for a given compound on any cell type. For this application, the clones corresponding to elements identified from cells used to establish banks specific for cell viability, as well as those specific for the induced deregulation, are hybridized with a probe derived from the untreated cells under study. Their hybridization serves as the reference RNA expression common to both the model of deregulation and the cell model under study. Comparison of RNA expression in the untreated cell situation with that of situations treated with different products at different concentrations and treatment times can be easily done by comparing the hybridization profiles of each probe from each situation under study. The toxicty index of a situation can be evaluated by assigning a value of 1 to clones that hybridize with the untreated probe and do not hybridize with the treated situation, on the one hand, and by also assigning a value of 1 to clones not hybridizing with the untreated probe but hybridizing with the treated probe, on the other hand. The index is then the sum of the individual 1 values expressed as a percentage of the number of clones subjected to hybridization. This index can therefore range from 0 to 100. This example of calculation of the toxicity index is not limiting. Other mathematical methods, algorithms or calculation processes such as neuronal networks can also be used.

The value of determining such an index by hybridizing clones derived from differential qualitative screening between two states of a same cell type (proliferation and apoptosis-induced) with probes from other cell types, is confirmed by the ability to determine an index that is all the greater for a given compound when the concentration applied to the test cells is high. Naturally, the value of the index depends on the threshold at which a clone is assigned a value of 1 or 0. The index is all the greater when the factor of repression or induction that the clone requires for consideration is low. The robustness of the method is nonetheless illustrated by the fact that there is a linear relation between the chosen factor and the calculated toxicity index. This linearity reflects the number of independent events which constitute the qualitative bank, which makes it possible to avoid giving too much weight to a particular clone with an overly high differential expression between the treated and untreated situation.

7. KITS

The present invention also concerns kits for the implementation of the aforementioned methods. The invention more specifically concerns kits for the study of the toxic potential of a test compound, comprising at least:

a nucleic acid bank corresponding to genetic events (transcriptional and/or splicing) characteristic of alteration(s) in one or more cell signalling pathways, notably situation(s) of deregulation of cell growth and/or viability.

The kits of the invention more generally comprise a bank of genetic markers characteristic of deregulation(s), for example apoptosis, such as defined in the invention, deposited on a solid support.

The kits of the invention more preferably comprise a nucleic acid bank characteristic of several situations of deregulation induced in different conditions.

According to another specific embodiment, the kits of the invention comprise at least one nucleic acid bank comprising clones corresponding to genetic events common to cells in a situation of deregulation and in a situation of toxicity.

In the kits according to the invention, the banks further advantageously comprise control clones for calibration of the detected signals. These controls can more particularly comprise three types of material:

genomic DNA clones, cDNA used for construction of probes that will hybridize the banks, and/or cDNA corresponding to mRNA encoding control proteins, for example housekeeping proteins (especially enzymes) such as □-actin or GAPDH (Glyceraldehyde Phosphate DeHydrogenase).

The controls provided by the housekeeping enzymes are classically used by those skilled in the art in cDNA display experiments However, during the deregulation phenomena according to the invention, the quantity of mRNA of these enzymes can vary. Therefore, to normalize the hybridizing power (and therefore the signal) of each probe, the present invention proposes the use of one or more other control systems. In this regard, the use of genomic DNA and/or cDNA (unlabelled) corresponding to the probe (i.e. to the DNA population from the treated or untreated biological sample) makes it possible, according to the invention, to obtain hybridization controls independent of any qualitative or quantitative variations in gene expression. Equivalent quantities of cDNA with the same specific activity after radiolabelling should in principle generate equivalent signals by hybridizing with both genomic DNA and with themselves.

The kits of the invention can also comprise:

oligonucleotides for use in the preparation of the probes, and/or a hybridization protocol, and/or items and information for establishment of a toxicity index for each test product, notably a signal processing software program.

The oligonucleotides are preferably semi-random, such as oligonucleotides with the formula X—$N_n$—AGGT, where X is a stabilizing sequence such as GAGAAGCGTTATG (SEQ ID NO: 1) or CCACGCTACAAG(C) (SEQ ID NO:2), N is a base, and n is a whole number between 3 and 8 inclusive.

The feasibility, realization and other advantages of the invention are depicted in further detail in the examples that follow, which should be considered illustrative and non-limiting.

8. EXAMPLE

8.1. Identification of Genetic Markers of Toxicity from Qualitative Screening on a Cellular Apoptosis System An example of the contribution of differential qualitative analysis to the identification of genetic markers associated with drug toxicity is given by the use of DATAS in a model of apoptosis induction via induction of wild type p53 expression. This cell model was established by transfection of a system of inducible expression of the p53 tumor suppressor gene. So as to identify the qualitative differences specifically related to p53 -induced apoptosis, qualitative screening was implemented on messenger RNA extracted from induced (mI) and non-induced (mNI) cells. This messenger RNA is converted to the complementary DNA (cI) and (cNI) using reverse transcriptase (RT) and biotinylated oligonucleotide primers. mI/cNI and cI/mNI hybrids are then obtained in liquid phase.

The required quantities of RNA and cDNA (in this case, 200 ng of each) are combined and ethanol-precipitated. The samples are taken up in 30 µl of hybridization buffer (40 mM Hepes pH 7.2, 400 mM NaCl, 1 mM EDTA) supplemented with deionized formamide (80% V/V). After denaturation for 5 min at 70° C., samples are incubated overnight at 40° C.

Streptavidin beads (Dynal) are washed and then reconditioned in binding buffer (2X=10 mM Tris-HCl pH 7.5, 2 M NaCl, 1 mM EDTA). Hybridization samples are adjusted to a volume of 200 µl with water and added to 200 µl of beads, then incubated at 30° C. for 60 min. The beads are captured on a magnet and washed, then suspended in 150 µl of RnaseH buffer and incubated at 37° C. for min. After capture on the magnet, non-hybridized regions are released in the supernatant which is treated with Dnase, then extracted with acidic phenol/chloroform and ethanol-precipitated. Ethanol precipitations of small quantities of nucleic acids are done with the commercial polymer SeeDNA (Amersham Pharmacia Biotech) for quantitative recovery of nucleic acids from very dilute solutions (ng/ml concentrations).

cDNA synthesis from the RNA samples derived via the action of RnaseH is carried out by using random hexanucleotides and Superscript II Reverse Transcriptase. The RNA is then degraded in a mixture of RnaseH and Rnase T1. The primer, unincorporated nucleotides and enzymes are separated from the cDNA on a myGlassMAX Spin cartridge. The cDNA corresponding to splicing loops is then used for PCR with semi-random oligonucleotides with the following structure: (FS3)N7AGGT, where (FS3)= CCACGCTACAAG (SEQ ID NO:3).

PCR is performed with taq polymerase for 30 cycles:

Initial denaturation : 94° C. for 1 min.

94° C. for 30 s

55° C. for 30 s

72° C. for 30 s

Final elongation : 72° C. for 5 min.

The PCR products are cloned in a pGEM-T vector (Promega) with a floating T at the 3' ends to facilitate cloning of fragments derived from the action of taq polymerase. Following transformation in competent JM109 bacteria (Promega), colonies are stored on 96 well plates. The PCR products generated with the T7 and Sp6 oligonucleotides located on the cloning plasmid and surrounding the insertion cassettes are deposited on nitrocellulose filters.

HepG2 cells are then individually treated with different compounds with different levels of toxicity. In this example, the concentration used was calculated by a cell viability test (MTT) and corresponds to an IC80. Table 1 gives the concentrations of the different compounds and the exposure times.

TABLE 1

| Compound | Concentration | Time |
| --- | --- | --- |
| Aspirin | 2 mM | 18 h |
| Paracetamol | 1 mM | 18 h |
| Cyclosporine | 2.5 µM | 18 h |
| Diclofenac | 50 µg/ml | 18 h |
| Beclomethazone | 50 nM | 18 h |
| Methotrexate | 500 nM | 18 h |
| Erythromycin | 2.5 µg/ml | 18 h |
| Vinblastine Sulfate | 30 µM | 18 h |
| Clonidine | 150 µM | 18 h |
| Valinomycin | 15 nM | 18 h |
| Etoposide | 50 µg/ml | 18 h |
| Camptothecin | 1 µg/ml | 4 h |
| PMA | 1 µg/ml | 18 h |
| Ethanol | 0.1 M/0.5 M | 4 h |
| 5 FU | 10 µM | 24 h |
| Cycloheximide | 5 µg/ml | 18 h |
| FCCP | 5 µM | 18 h |
| Staurosporine | 50 nM | 18 h |
| Terbutaline Sulfate | 200 ng/ml | 18 h |
| Epinephrine Hydrate | 50 µg/ml | 18 h |
| AZT | 50 µg/ml | 18 h |
| H2O2 | 0.1 mM | 18 h |
| Actinomycin D | 0.02 µg/ml | 18 h |

Labelled RNA probes are prepared from these situations. To do so, the first cDNA strand obtained from total RNA by methods known to those skilled in the art serves as matrix for the PCR reaction using the oligonucleotides (FS4) GN3AGGT and FS3CN3AGGT, in which (FS4) GAGAAGCGTTAT (SEQ ID NO:4), according to the following program:

Initial denaturation: 95° C. for 5 min
5 cycles with: denaturation : 94° C. for 30 sec
 annealing: 30° C. for 30 sec
 temperature increase from 30 to 72° C. in 30 sec
 elongation: 72° C. for 30 sec
35 cycles with: denaturation: 94° C. for 30 sec
 annealing: 57° C. for 30 sec
 elongation: 72° C. for 30 sec
Final elongation: 72° C. for 7 min The PCR products are labelled with the Redyprime kit (Amersham).

Figure 1:
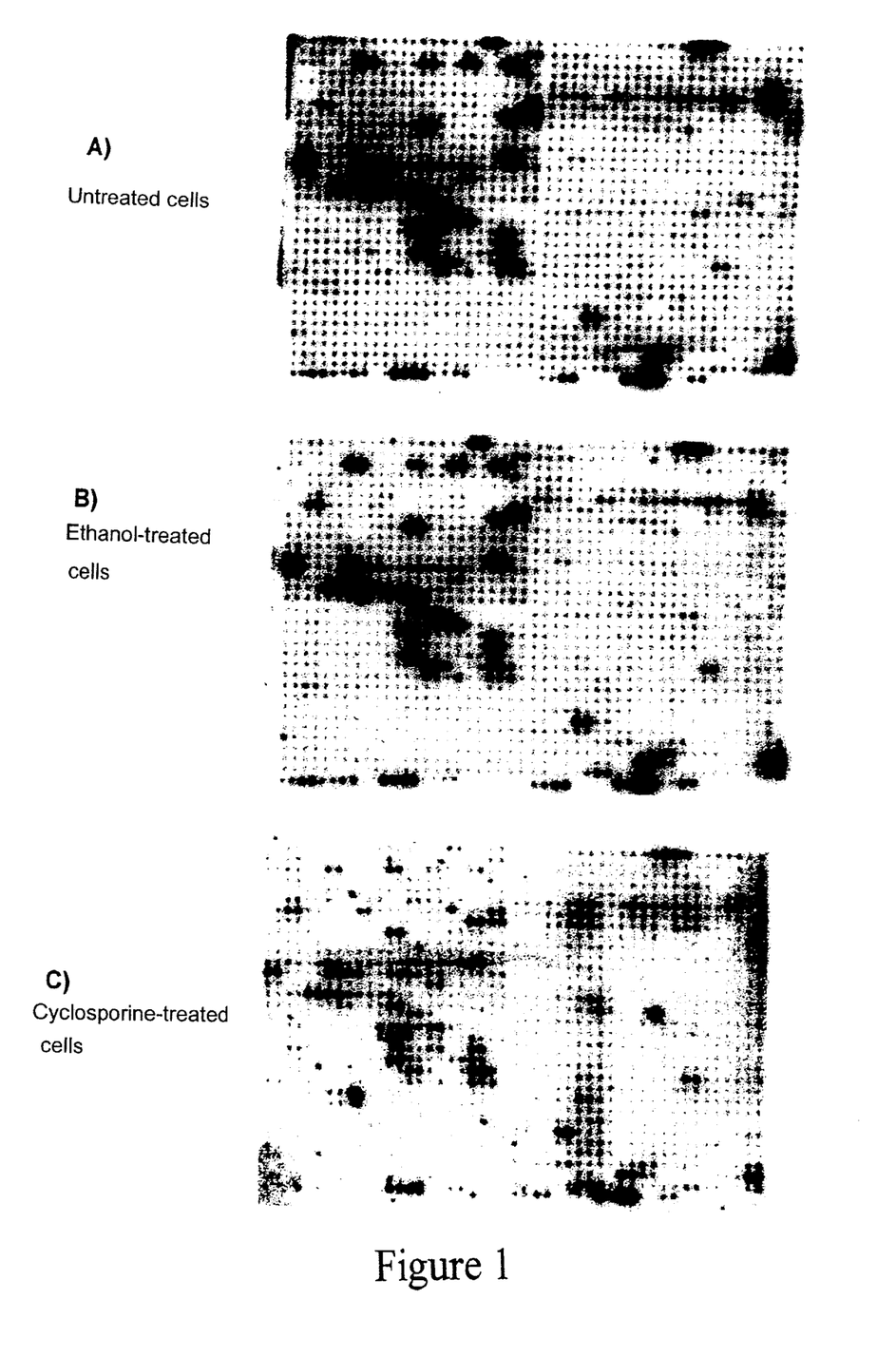
FIG. 1. Differential hybridization of probes from HepG2 cells untreated (A), treated with ethanol (B) or treated with cyclosporine on filters containing PCR fragments corresponding to clones from the qualitative screening of a p53 -induced apoptosis system.

Filters are prehybridized in hybridization buffer (Rapid Hybrid Buffer, Amersham) containing 100 µg/ml of salmon sperm DNA at 65° C. for 30 min. The PCR probe is then applied to the membrane ($0.5 \times 10^6$ to $1 \times 10^6$ cpm/ml) and incubated at 65° C. for 2 to 18 hours. Filters are washed in 5xSSC buffer, 0.1% SDS at 65° C. for 30 min then in 0.2xSSC buffer, 0.1% SDS. The hybridization profiles are analyzed by measuring the radioactivity with an InstantImager (Packard Instruments) (FIG. 1). Quantification of the individual hybridization intensities allows calculation of an index according to the procedure described above (FIG. 2). This result shows that it is possible to classify different products according to their ability to induce the expression of markers that are differentially spliced during p53 -induced toxicity. For example, in HepG2 cells, diclofenac generates more splicing events identical to those induced by p53 -related toxicity than aspirin. The use of banks containing cDNA sequences differentially spliced in a reference (healthy) situation and a situation involving a major route of toxicity, therefore enables the classification of products whose actions are not distinguishable using standard toxicity tests such as MTT.

8.2. Identification of Genetic Markers of Toxicity from Qualitative Screening on Tumor Biopsies A second example of the use of the invention for the identification of genetic markers of toxicity consists in the generation of differential nucleic acid banks for healthy tissue and tumor tissue. The value of identifying sequences specifically expressed in control (healthy) tissue on the one hand, and in tumor tissue on the other hand, is related to the fact that within a tumor, information characteristic of deregulated cell growth and cell death is present in different cells but also within the same cells. As compared to a model of apoptosis induced by deregulated expression of p53 or any other protein with a negative effect on cell growth and viability, the use of tumor specimens therefore additionally provides filters for use in predictive toxicology bearing sequences whose expression is characteristic of cellular hyperproliferation or carcinogenesis.

The working material comprised tumor biopsy specimens from 7 patients with head and neck cancers together with biopsy specimens from healthy uvula of these same patients. The procedure was identical to that described in example 8.1 although this is not a quantitative considering the scarcity of material available from human biopsy specimens.

The nucleic acid fragments generated by application of the invention to tumor and normal tissues were deposited on nitrocellulose filters. These filters were hybridized with the same radioactive probes as those used in example 8.1, i.e. generated from the genetic material of HepG2 cells treated with different compounds displaying different toxic potential. Differential hybridization profiles were observed for the different compounds, thereby demonstrating the utility of these nucleic acid banks for evaluation of the toxicity of a given compound.

Figure 3:
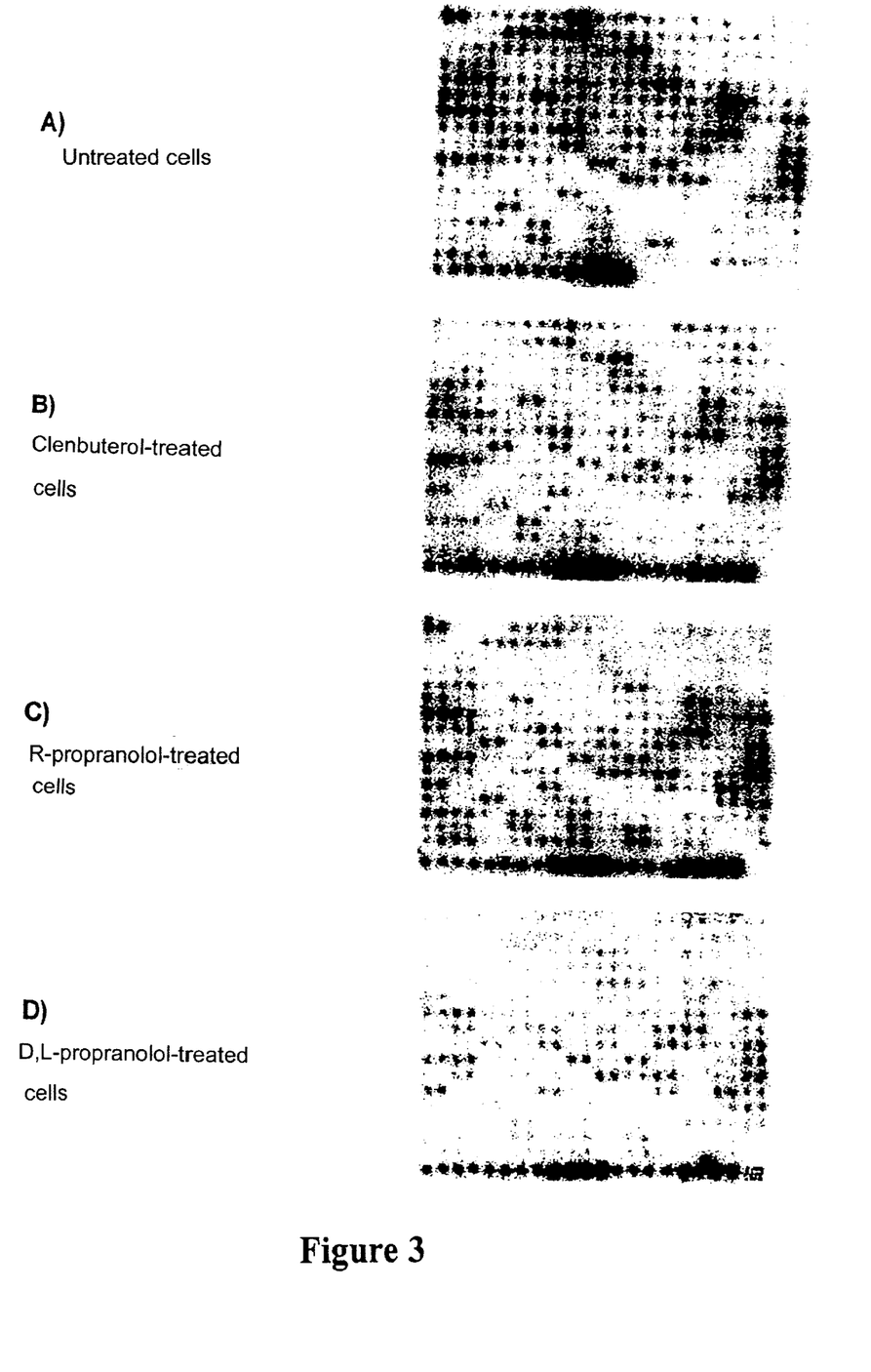
FIG. 3. Differential hybridization of probes from HepG2 cells untreated (A), treated with clenbuterol (B), R-propranolol (C) or D,L-propranolol (D) on filters containing PCR fragments corresponding to clones from the qualitative screening of tumor biopsies.

FIG. 3 depicts the hybridization signals obtained with probes derived from normal HepG2 cells, or cells treated with clenbuterol, the inactive propranolol enantiomer, or a racemic mixture of the active and inactive propranolol enantiomers. The compounds were used at the concentrations indicated in Table 1 and the hybridization probes and protocols were identical to those in the paragraph describing the use of filters containing specific signatures of p53 -induced apoptosis (example 8.1).

Figure 2:
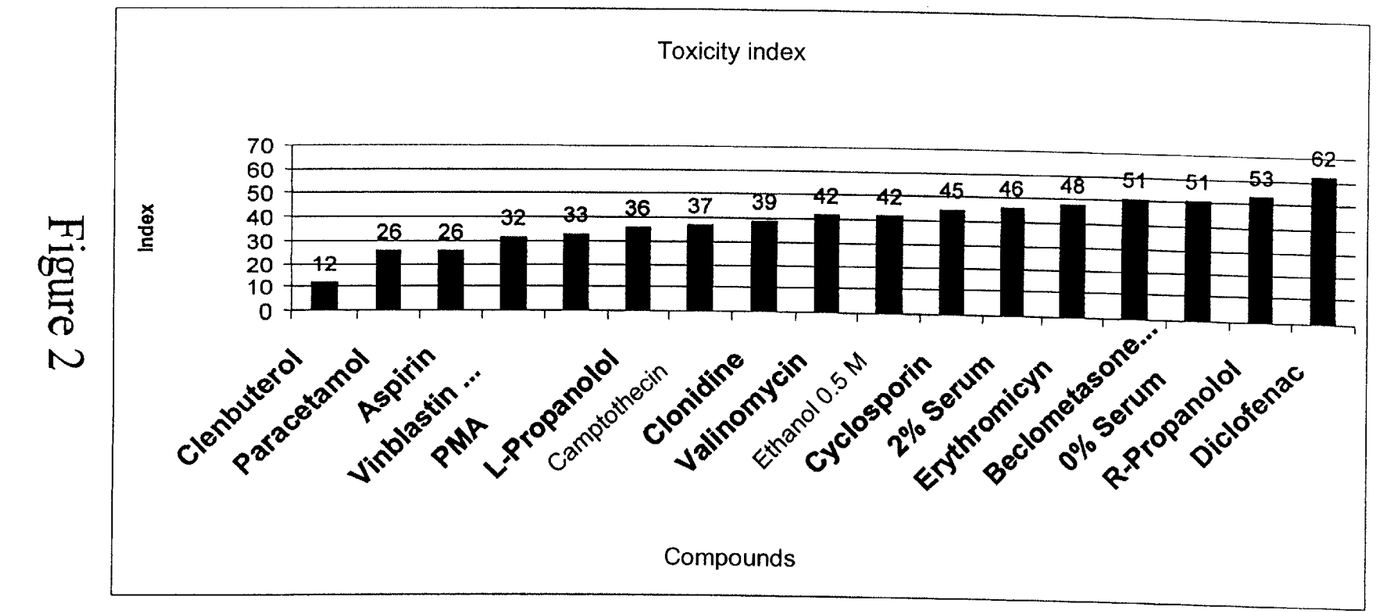
FIG. 2. Toxicity index calculated for different toxic compounds on the p53 apoptosis filter.

The hybridization signals shown in FIG. 3 can be quantified and serve as a basis for determining a toxicity index for each compound using the same procedure as that used to obtain the indices shown in FIG. 2. Thus, the hybridizations shown in FIG. 3 reveal that the effects of the different compounds on HepG2 cells, which cannot be distinguished by standard toxicological methods such as MTT staining, can be classified according to their ability to mobilize splicing events specific for the differences that exist between cells from healthy tissue and tumor cells.

What is claimed is:

1. A method of analysis of the toxic potential, in a human or murine cell, of a test compound, said method comprising:
   (a) contacting, under conditions allowing hybridization to occur,
      (i) a nucleic acid sample from human or murine cells treated with a candidate therapeutic molecule selected from a peptide, a polypeptide, a nucleic acid, a lipid, a carbohydrate, a chemical molecule and a plant extract and
      (ii) a library of nucleic acids, wherein said library comprises, immobilized on a support, nucleic acid molecules comprising a sequence specific for genes or for splicing forms of genes, the expression of said genes or splicing forms being induced in a human or murine cell having a deregulated p53 gene expression or a deregulated p53 cell signalling pathway, and
   (b) analysing the hybridization profile between said nucleic acid sample and said library to determine the toxic potential of the candidate therapeutic molecule.

2. The method according to claim 1, wherein the nucleic acid sample a) comprises messenger RNA molecules from said treated human or murine cells.

3. The method according to claim 1, wherein the nucleic acid sample a) comprises cDNA or cDNA fragments prepared from RNA molecules of said treated human or murine cells.

4. The method according to claim 1, wherein the nucleic acid sample a) comprises amplification products.

5. The method according to claim 1, wherein the nucleic acid sample a) is labelled by radioactive, fluorescent, enzymatic or colorimetric labels.

6. The method of claim 1, wherein the library comprises a plurality of different nucleic acids comprising a sequence complementary to at least a portion of a gene that is regulated by a modification in p53 gene expression in a human or murine cell.

7. The method of claim 6, wherein the library comprises a plurality of different nucleic acids comprising a sequence complementary to at least a portion of a gene that is regulated by an increased wild-type p53 gene expression in a human or murine cell.

8. The method of claim 7, wherein the library comprises a plurality of different nucleic acids comprising a sequence complementary to at least a portion of a gene that is induced by an increased wild-type p53 gene expression in a human or murine cell.

9. The method of claim 7, wherein the library comprises a plurality of different nucleic acids comprising a sequence complementary to at least a portion of a gene that is spliced in a human or murine cell with increased wild-type p53 gene expression.

10. A method of analysis of the toxic potential, in a human or murine cell, of a test compound, said method comprising:

(a) separately contacting, under conditions allowing hybridization to occur,
   (i) labelled nucleic acid probes corresponding to RNA molecules (1) from human or murine cells treated with a candidate therapeutic molecule selected from a peptide, a polypeptide, a nucleic acid, a lipid, a carbohydrate, a chemical molecule and a plant extract, and (2) from untreated human or murine cells and
   (ii) a library of nucleic acids, wherein said library comprises, immobilized on a support, nucleic acid molecules comprising a sequence specific for genes or for splicing forms of genes, the expression of said genes or splicing forms being induced in a human or murine cell having a deregulated p53 gene expression or a deregulated p53 cell signalling pathway, and (b) analysing the hybridization profile between said probes and said library to determine the toxic potential of the candidate therapeutic molecule.

11. The method according to claim 1 or 10, wherein the test compound is an individual compound or is present in a mixture with other substances.

12. The method according to claim 1 or 10, wherein the nucleic acid library b) comprises nucleic acids having a sequence complementary to at least a portion of a gene that is induced by an increased wild-type p53 gene expression in a human or murine cell and nucleic acids having a sequence complementary to at least a portion of a gene that is spliced in a human or murine cell with increased wild-type p53 gene expression.

13. The method according to claim 1 or 10, wherein the treated or untreated human or murine cells are cell lines.

14. The method according to claim 1 or 10, wherein the treated or untreated human or murine cells are primary cultures.

15. The method according to claim 10, wherein the nucleic acid probes a) correspond to messenger RNA molecules from treated and untreated human or murine cells.

16. The method according to claim 10, wherein the nucleic acid probes a) are cDNA or cDNA fragments prepared from the RNA molecules of treated and untreated human or murine cells.

17. The method according to claim 10, wherein the nucleic acid probes a) are amplification products.

18. The method according to claim 10, wherein the nucleic acid probes a) are labelled by radioactive, fluorescent, enzymatic or calorimetric labels.

19. The method according to claim 15 or 16, wherein the nucleic acid library b) is prepared by (i) hybridizing a first nucleic acid population from a human or murine cell having a deregulated p53 gene expression or p53 cell signalling pathway and a second nucleic acid population from a human or murine cell not having having a deregulated p53 gene expression or a deregulated p53 cell signalling pathway, and (ii) separating, from the hybrids formed in (i), nucleic acids comprising an unpaired region.

20. The method of claim 10, wherein the library comprises a plurality of different nucleic acids comprising a sequence complementary to at least a portion of a gene that is regulated by a modification in p53 gene expression in a human or murine cell.

21. The method of claim 20, wherein the library comprises a plurality of different nucleic acids comprising a sequence complementary to at least a portion of a gene that is regulated by an increased wild-type p53 gene expression in a human or murine cell.

22. The method of claim 21, wherein the library comprises a plurality of different nucleic acids comprising a sequence complementary to at least a portion of a gene that is induced by an increased wild-type p53 gene expression in a human or murine cell.

23. The method of claim 21, wherein the library comprises a plurality of different nucleic acids comprising a sequence complementary to at least a portion of a gene that is spliced in a human or murine cell with increased wild-type p53 gene expression.

24. A method of determining the toxic potential, in a human or murine cell, of a test compound, said method comprising separately contacting, under conditions allowing hydridisation to occur:

labelled nucleic acid probes corresponding to mRNA molecules from untreated human or murine cells and a library of immobilized nucleic acids, wherein the library comprises a plurality of different nucleic acids comprising a sequence complementary to at least a portion of a gene that is regulated by an increased wild-type p53 gene expression in a human or murine cell, and labelled nucleic probes corresponding to mRNA molecules from human or murine cells treated with a candidate therapeutic molecule selected from a peptide, a polypeptide, a nucleic acid, a lipid, a carbohydrate, a chemical molecule and a plant extract, and said nucleic acid library, the hybridization profile indicating the toxic potential of the candidate therapeutic molecule.

25. The method according to claim 24, wherein the nucleic acid library comprises a plurality of different nucleic acids characteristic of tumor cells.

* * * * *

SEQUENCE LISTING

```
<160> NUMBER OF SEQ ID NOS: 4

<210> SEQ ID NO 1
<211> LENGTH: 13
<212> TYPE: DNA
<213> ORGANISM: Artificial Sequence
<220> FEATURE:
<223> OTHER INFORMATION: Synthetic primers

<400> SEQUENCE: 1
gagaagcgtt atg                                                          13

<210> SEQ ID NO 2
<211> LENGTH: 13
<212> TYPE: DNA
<213> ORGANISM: Artificial Sequence
<220> FEATURE:
<223> OTHER INFORMATION: Synthetic primers

<400> SEQUENCE: 2
ccacgctaca agc                                                          13

<210> SEQ ID NO 3
<211> LENGTH: 12
<212> TYPE: DNA
<213> ORGANISM: Artificial Sequence
<220> FEATURE:
<223> OTHER INFORMATION: Synthetic primers

<400> SEQUENCE: 3
ccacgctaca ag                                                           12

<210> SEQ ID NO 4
<211> LENGTH: 12
<212> TYPE: DNA
<213> ORGANISM: Artificial Sequence
<220> FEATURE:
<223> OTHER INFORMATION: Synthetic primers

<400> SEQUENCE: 4
gagaagcgtt at                                                           12
```